United States Patent [19]

Jensen

[11] Patent Number: 4,938,749
[45] Date of Patent: Jul. 3, 1990

[54] OSTOMY POUCH FILTER HOUSING

[75] Inventor: Ole R. Jensen, River Vale, N.J.

[73] Assignee: E. R. Squibb & Sons, Inc., Princeton, N.J.

[21] Appl. No.: 242,343

[22] Filed: Sep. 9, 1988

[51] Int. Cl.$^5$ .............................................. A61F 5/44
[52] U.S. Cl. ................................... 604/333; 55/385.4
[58] Field of Search ............................. 604/332–345; 55/385.4, 417

[56] References Cited

U.S. PATENT DOCUMENTS 4,411,659 10/1983 Jensen ................................... 604/333
4,451,258 5/1984 Jensen ................................. 55/385.4

FOREIGN PATENT DOCUMENTS 2177301 1/1987 United Kingdom .

Primary Examiner—Jerome L. Kruter
Attorney, Agent, or Firm—James & Franklin

[57] ABSTRACT

The housing is mounted on and sealed around an opening in the pouch wall. The disc-like base of the housing has a central, axially extending entrance passageway aligned with the pouch opening. A portion of the base extends radially outwardly beyond the seal and has a second axial passageway therethrough. The cover of the housing defines a filter receiving recess aligned with the entrance passageway. The recess has a connecting channel extending radially therefrom. The cover is removably mounted on the base for relative rotational movement between a first position in which the connecting channel aligns with the exit passageway, so as to permit venting of the gases from the pouch, and a second position wherein the connecting channel is out of alignment with the exit passageway, closing the vent.

16 Claims, 4 Drawing Sheets

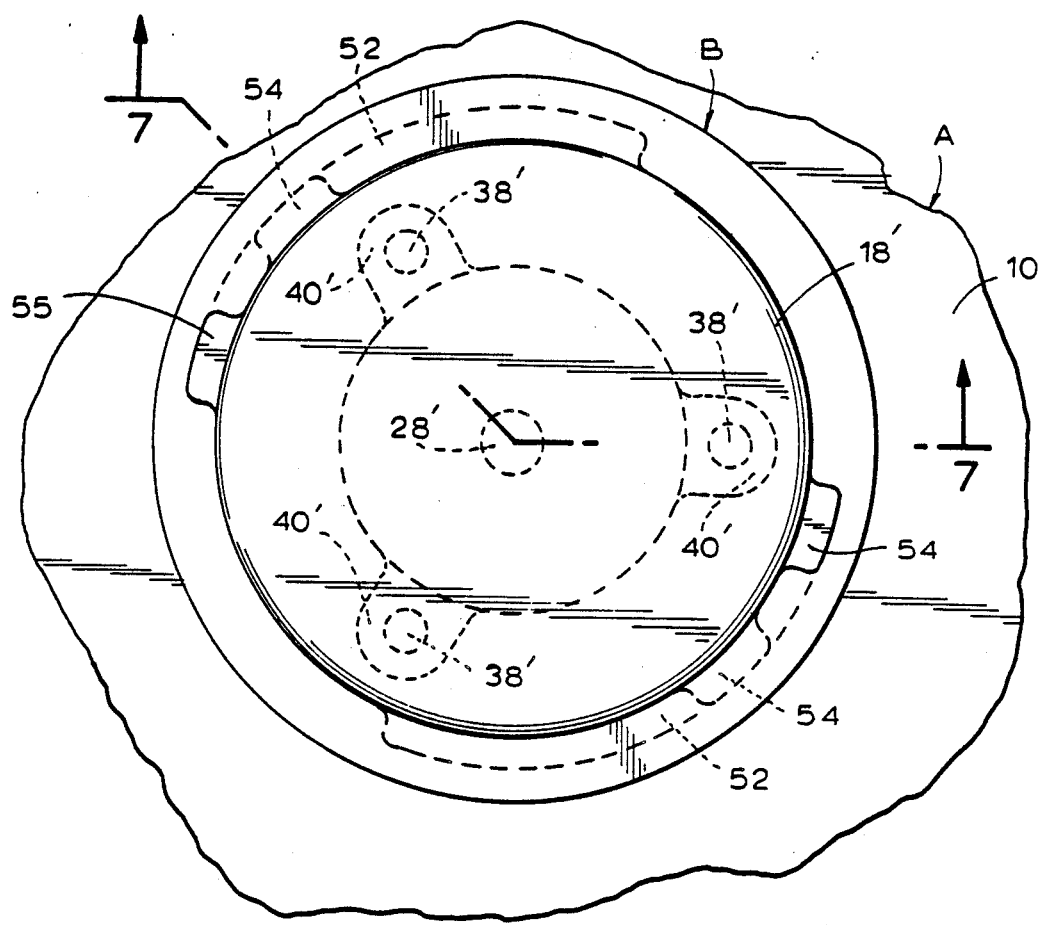
F I G. 6
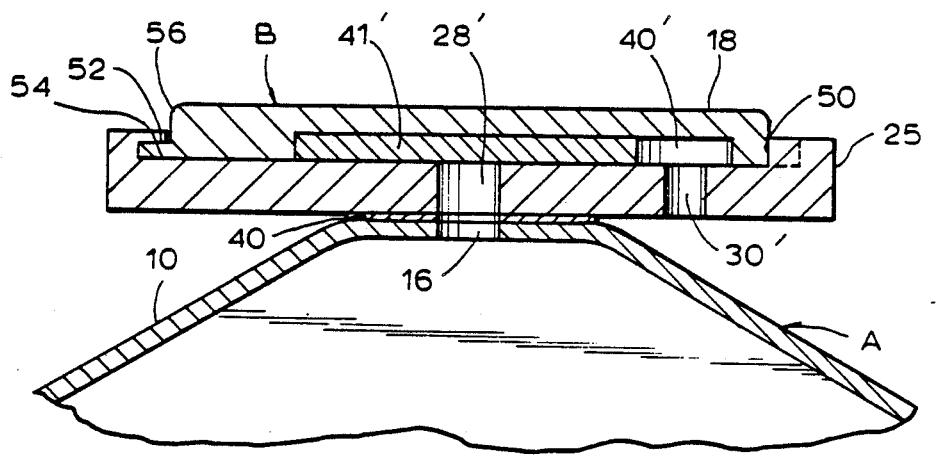
F I G. 7

2

OSTOMY POUCH FILTER HOUSING

BACKGROUND OF THE INVENTION

The present invention relates to ostomy pouches and more particularly to a filter housing designed for use with an ostomy pouch or the like.

Ostomy pouches of various types are designed for use by individuals who have undergone ileostomy or colostomy surgery and hence have a stoma or artificial opening formed in the abdominal wall which serves as a discharge outlet for waste material. The ostomy pouch is affixed to the patient's abdomen over the stoma so as to collect the waste material as it is discharged. In order to prevent the escape of liquid or solid waste from the ostomy pouch, it is necessary that the fluid tight seal be maintained between the pouch and the skin surrounding the stoma.

Certain problems occur as a result of the fluid tight seal. Discharge of gas from the intestines through the stoma causes the pouch to become inflated. The inflation of the pouch, which is normally visually inconspicuous, may cause embarrassment to the wearer as the pouch becomes noticeable, even through clothing. The pressure created by the gas in the pouch, if it is not allowed to escape, may build up to the point where it causes accute discomfort. In the extreme situation, a high enough pressure may cause the fluid tight seal between the pouch and the skin to be disrupted, releasing odors and possibly waste material.

In order to overcome the problems associated with the accumulation of gases within the pouch, pouches have been designed with various types of vents which control the release of the gas. In addition, such vents have been used in conjunction with deodorizing filters through which the gas must pass as it is vented.

DESCRIPTION OF RELATED ART

In at least one structure, disclosed in my U.S. Pat. No. 4,451,258 issued May 29, 1984 and entitled "Ostomy Bag With An Adjustable Vent", the flow rate of the gas through the filter can be varied to enhance the effectiveness of the filter and permit precise control over the degree of inflation of the bag. My patented device requires a coupling part to be situated within the interior of the pouch so as to connect with an externally mounted base. Rotation the base, relative to the coupling part, causes a channel in the stem of the base, which stem is adapted to be received in a recess in the internal coupling part so as to puncture the pouch wall, to align with a passageway. This alignment permits passage of gas from the interior of the pouch through a filter. The angular position of the base relative to the internal coupling part controls the degree of venting.

While it has been found that my patented device functions excellently, it requires that the coupling part be situated within the interior of the pouch. The device itself is somewhat complex and hence relatively expensive to manufacture. Moreover, while it provides highly accurate control over the flow rate through the filter, a simpler structure is probably sufficient for most purposes.

It is, therefore, a prime object of the present invention to provide an ostomy pouch filter housing which has a simple construction and hence can be manufactured inexpensively.

It is another object of the present invention to provide an ostomy pouch filter housing which is designed to be mounted externally to the pouch wall.

It is another object of the present invention to provide an ostomy pouch filter housing designed to be mounted on the pouch wall through the use of a ring weld or adhesive.

It is another object of the present invention to provide an ostomy pouch filter housing which includes a removable cover and either snap-fit or bayonet-type mounting means.

It is another object of the present invention to provide an ostomy pouch filter housing which is rotatable relative to a base to open or close a gas venting passageway.

SUMMARY OF THE INVENTION

In accordance with the present invention, a filter housing is provided for mounting on an ostomy pouch or the like of the type having a wall with an opening. The housing comprises a base with an entrance passageway. The base is sealed to the external surface of the wall surrounding the opening with the entrance passageway aligned with the opening. The base has a portion which extends outwardly beyond the seal. An exit passageway is provided through the outwardly extending portion of the base. A cover is provided having a filter receiving recess aligned with the entrance passageway. A connecting channel extends from the recess through the cover. The cover is removably mounted on the base for relative movement between a first position in which the connecting channel aligns with the exit passageway and a second position wherein the connecting channel is out of alignment with the exit passageway.

Preferably, the base has a disc-like configuration and the entrance passageway extends substantially axially through the base. Preferably, the entrance passageway is substantially centrally located on the base. The exit passageway is preferably substantially parallel to the entrance passageway.

The connecting channel preferably extends substantially radially within the cover. The filter receiving recess is preferably substantially circular in configuration.

The base is preferably composed of substantially rigid plastic material. Means are provided for removably mounting the cover on the base. The cover is preferably substantially composed of relatively flexible material and the removable mounting means preferably comprises means for snap fitting the cover on the base. Alternatively, the removable mounting means may comprise bayonet locking means.

In its most preferred embodiment, a plurality of connecting channels radially extend from the filter receiving recess. A plurality of exit passageways are provided. Each passageway is positioned to align with a different one of the radially extending connecting channels in the first rotatable position of the cover. Hence, multiple vents are achieved.

BRIEF DESCRIPTION OF THE DRAWINGS

To these and such objects which may hereinafter appear, the present invention relates to an ostomy pouch filter housing as set forth in detail in the following specification and recited in the annexed claims, taken together with the accompanying drawings in which like numerals refer to like parts and in which:

FIG. 6 is a top cut away view of a second embodiment of the present invention thereof which includes a bayonet type mounting.

FIG. 7 is a cross-sectional view of the second preferred embodiment of the present invention taken along line 7—7 of FIG. 6.

DESCRIPTION OF THE PREFERRED EMBODIMENTS

The figures disclosed two embodiments of the present invention. The first embodiment, illustrated in FIGS. 2, 3, 4 and 5, has a cover member which is made of flexible material so as to snap-fit onto the rigid base member. The second embodiment, as disclosed in FIGS. 6 and 7, has a substantially rigid cover member which has a bayonet-type mounting configuration. Since the parts of the two embodiments are quite similar in structure, corresponding parts have been given the same numbers, with primes added to the numbers of the second embodiment.

Figure 1:
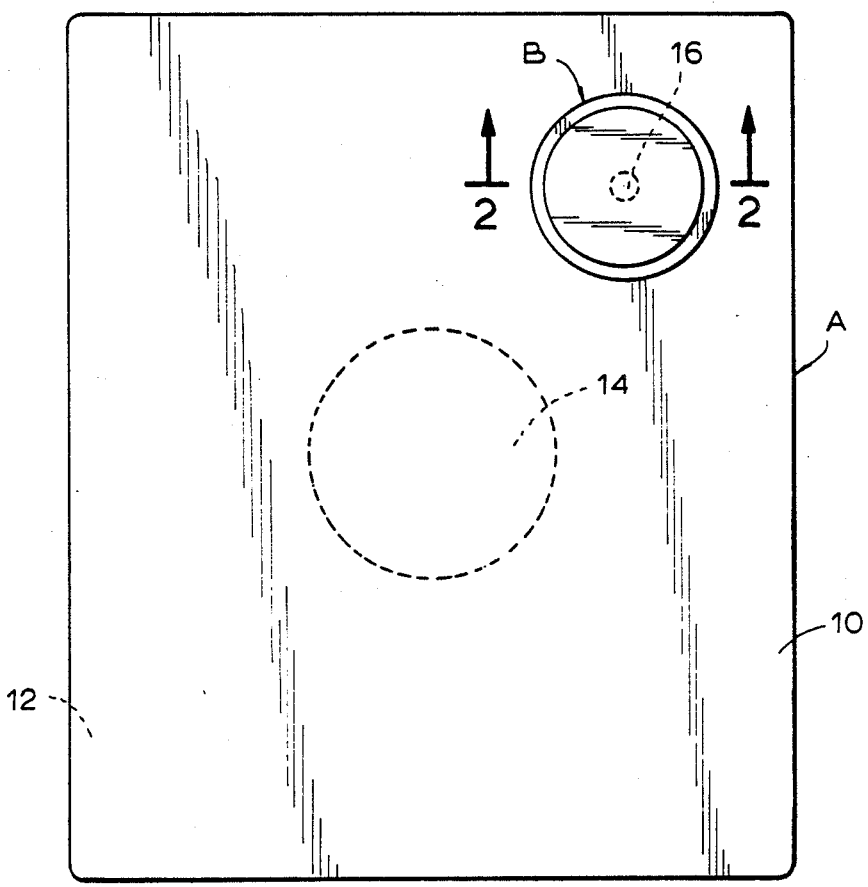
FIG. 1 is a plan view of a typical ostomy pouch showing the filter housing of the present invention affixed thereto.

As shown in FIG. 1, a typical ostomy pouch, generally designated A, includes a front wall 10 and a rear wall 12 made of thin flexible, transparent or translucent plastic material which are sealed along the periphery to form a fluid type enclosure. At a central location within rear wall 12 is a circular stoma receiving opening 14 which may be defined by a rigid or semi-rigid coupling ring (not shown). This ring is designed to be removably attached to a mating coupling ring affixed to an adhesive backed label (not shown) which is adapted to adhere to the skin of the patient surrounding the stoma. While a typical pouch A is illustrated for purposes of explanation, it should be understood that the structure of the pouch itself forms no portion of the present invention.

The front wall 10 of the pouch is provided with a second, much smaller circular opening 16 which may be situated anywhere on the pouch, but is shown in FIG. 1 as being proximate the upper right hand corner. Over opening 16 is mounted the filter housing of the present invention, generally designated B. Housing B includes two parts, a cover member 18 and a base member 20.

Figure 2:
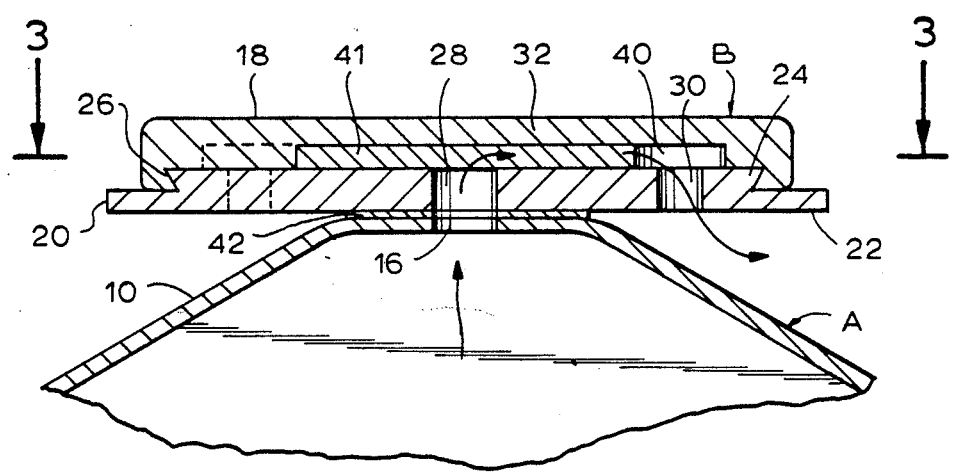
FIG. 2 is a cross-sectional view taken along lines 2—2 of FIG. 1 illustrating the first preferred embodiment of the present invention.
Figure 5:
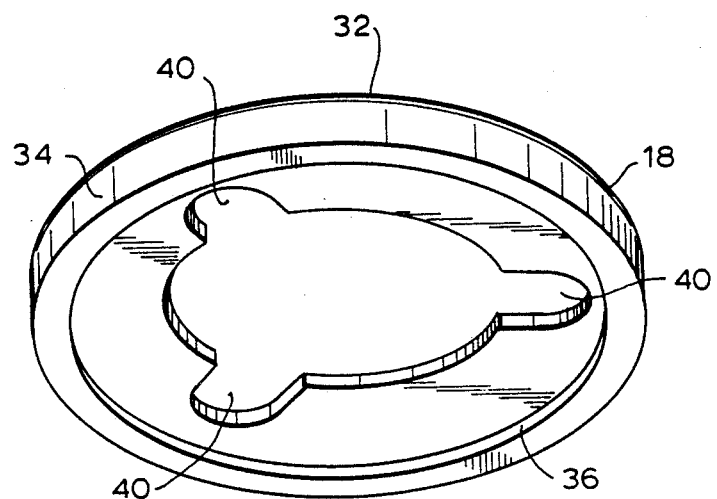
FIG. 5 is an exploded isometric view of the housing of the present invention.
Figure 5:
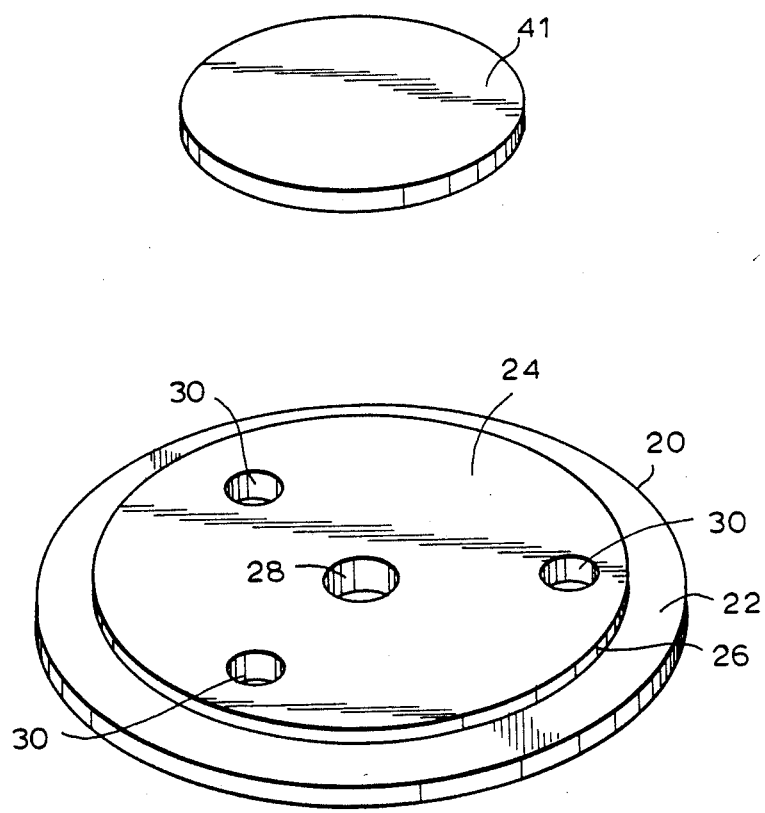

As best seen in FIGS. 2 and 5, base member 20 has a substantially disc-like structure with a lower portion 22 and upper portion 24. Lower portion 22 extends radially outwardly of upper portion 24. Between the surface of lower portion 22 and the surface of upper portion 24, is an upstanding wall 26 which, as best seen in FIG. 2, is inclined radially outwardly from lower portion 22 to upper portion 24.

Base member 20 is provided with a central axially extending entrance passageway 28 and three exit passageways 30 which are radially offset from passageway 28 and preferably arranged with substantially equal circumferential spacing. Exit passageways 30 extend in a direction substantially parallel to entrance passageway 28 and hence also extend axially with respect to the base member.

Cover member 18 is made of substantially flexible material such as plastic and includes a top surface 32 with a downwardly extending wall 34 so as to form a recess within which upper portion 24 of base member 20 is adapted to be received. The inner surface 36 of wall 34 is inclined in a direction substantially opposite to the direction of inclination of wall 26 on base member 20 so as to mate therewith, as best seen on FIG. 2, when cover 18 is snap-fitted into place with respect to member 20.

Cover member 18 is provided with a centrally located substantially circular filter receiving recess 38 within which a disc-like filter member 41 is adapted to be received. Recess 38 has three connecting passageways 40 which extend in a radial direction a distance from the central axis of cover member 18 greater than the distance between exit passageways 30 and the axis of base member 20.

Referring back to FIG. 2, the inner central portion of the undersurface of base member 20 is adapted to be sealingly affixed to the portion of pouch wall 10 which surrounds opening 16 so as to form a ring like fluid tight seal therewith. While FIG. 2 shows the seal as being formed by a layer of adhesive 42, it should be understood that this seal can be formed by any conventional means, such as heat welding, sonic welding or hot melt methods. It is important to proper functioning of the device that the ring seal 42 not extend outwardly from opening 16 to the extent that the exit passageways 30 are blocked.

Figure 3:
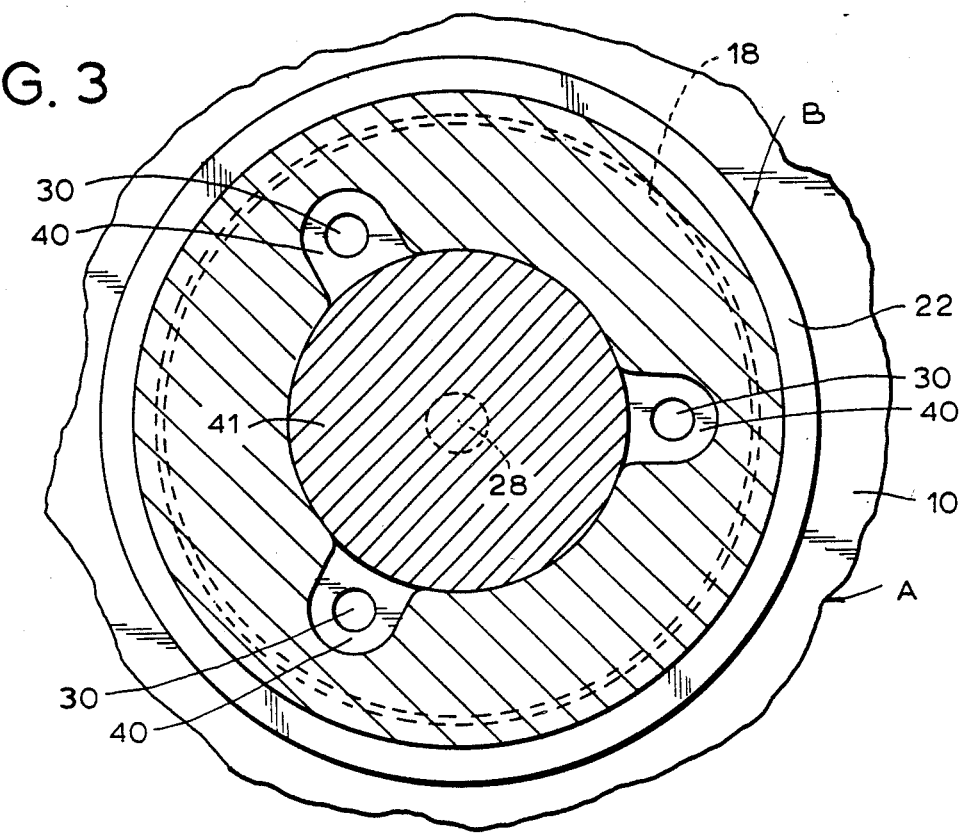
FIG. 3 is a top cut away view taken along line 3—3 of FIG. 2 showing the cover member in the vent position.
Figure 4:
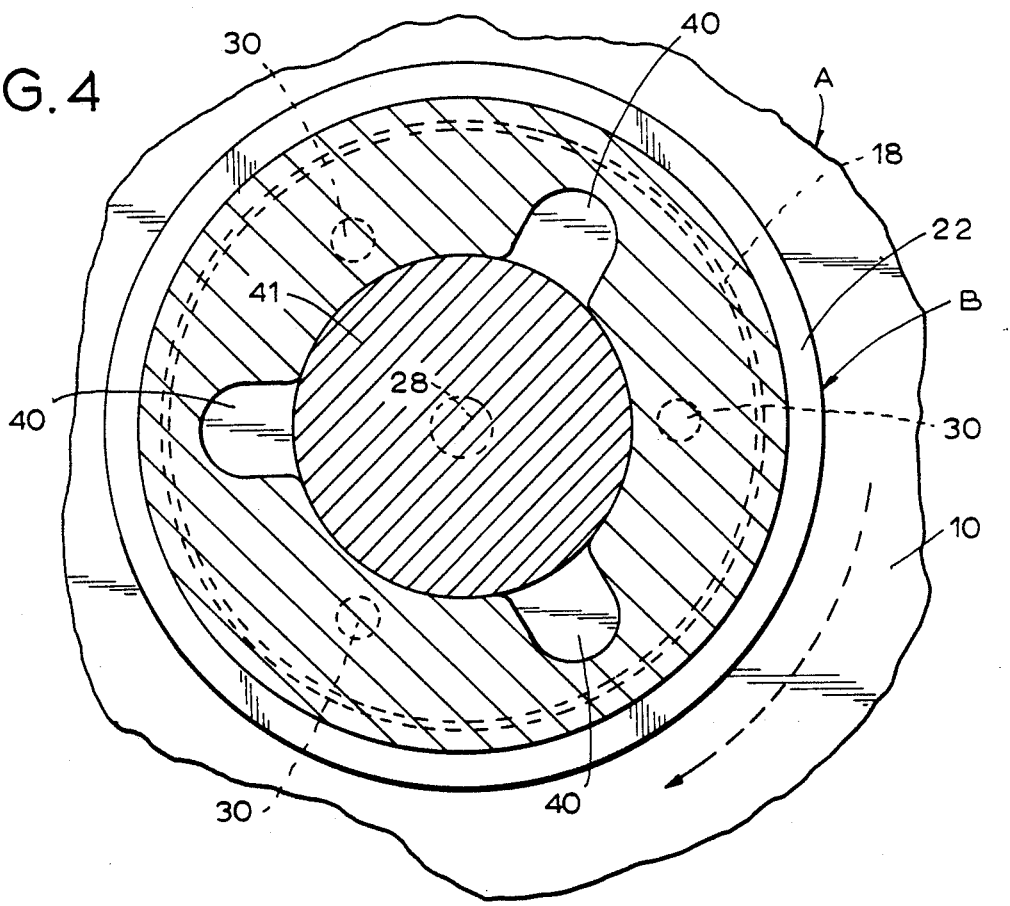
FIG. 4 is a view similar to that of FIG. 3 but showing the cover member in the closed position.

Referring now to FIGS. 3 and 4, FIG. 3 shows cover member 18 and base member 20 in the relative rotational position shown in FIG. 2, that is, in the venting position where connecting channels 40 in cover member 18 align with exit passageways 30 in base member 20 such that gases within pouch A can exit through central opening 16, pass through entrance passageway 28 and into the center of filter member 41. The gases then travel radially through the length of filter member 41, escape from the outer edge of the filter into the connecting channels 40 and then out exit passageways 30, as shown by the arrows of FIG. 2.

FIG. 4 shows the cover member 18 and base member 20 in a second relative rotational position where connecting passageways 40 are out of alignment with exit passageways 30. In this position, no venting of the gases is possible.

FIGS. 6 and 7 illustrate a second preferred embodiment of the present invention which, as noted above, is essentially the same as the first preferred embodiment except for the means for mounting cover member 18' to base member 20'. In this embodiment, cover member 20', instead of having a step-like configuration, is provided with a cover receiving recess 50. Recess 50, as best seen in FIG. 6, has oppositely situated arcuate recesses 52 designed to accept protrusions 54 which extend radially outwardly from the outer wall 56 of cover member 18'. The surface of base member 20' is provided with openings 55 such that protrusions 54 can be received within recesses 50. This permits cover member 18' to be removably mounted on base member 20' in bayonet-type fashion.

The length of recesses 52 permits cover member 18' to be rotated with respect to base member 20' through an angle of approximately 75 to 80 degrees. This permits connecting passageways 40' to align with passageways 38' to permit venting, in one position, as shown in FIGS. 6 and 7. In a second rotational position (not shown), the passageways are out of alignment and venting is prevented.

The cover member 18' can be clearly marked with indications showing the "open" and "closed" positions. These positions are preferably offset from the position which permits the cover member to be removed from the base member to permit replacement of the filter member 41. Suitable detents can be utilized such that the angular range of movement between the "open" and "closed" positions can be clearly distinguished by feel from the angular position necessary to remove the cover member.

It should now be appreciated that the present invention relates to a filter housing design for exterior mounting on an ostomy pouch or the like which has a wall with an opening. The housing has a simple construction and hence can be manufactured relatively inexpensively. No internal parts are required to mount the housing. Only a simple ring seal is required. A removable cover member is provided either with a snap-fit or bayonet-type mounting. Relative rotation of the cover member with respect to the base member causes opening and closing of the gas venting passageways.

While only a limited number of preferred embodiments have been disclosed herein for purposes of illustration, it is obvious that many variations or modifications can be made thereto. It is intended to cover all these variations and modifications which fall within the scope of the present dimension as defined by the following claims:

I claim:

1. A filter housing for mounting on an ostomy pouch having a wall with an opening comprising a base having a surface with an entrance passageway, said base surface facing and being sealed to the external surface of the pouch wall surrounding the opening with said entrance passageway aligned with the opening, said base surface having a portion which extends substantially laterally in the plane of said base outwardly beyond the seal, an exit passageway through said laterally outwardly extending portion of said base surface portion such that the gasses being filtered will exit in a direction substantially toward the pouch wall and a cover having a filter receiving recess adapted to align with said entrance passageway and a connecting channel extending from said recess, said cover being mounted on said base for relative movement between a first position in which said connecting channel aligns with said exit passageway and a second position at which said connecting channel is remote from said exit passageway.

2. The housing of claim 1 wherein said base has a disk-like configuration.

3. The housing of claim 2 wherein said entrance passageway extends substantially axially through said base.

4. The housing of claim 2 wherein said entrance passageway is substantially centrally located on said base.

5. The housing of claim 3 wherein said exit passageway is substantially parallel to said entrance passageway.

6. The housing of claim 3 wherein said connecting channel extends substantially radially within said cover.

7. The housing of claim 1 wherein said recess is substantially circular.

8. The housing of claim 1 wherein said base is composed of substantially rigid material.

9. The housing of claim 1 further comprising means for removably mounting said cover to said base.

10. The housing of claim 9 wherein said cover is composed of relatively flexible material and wherein said removable mounting means comprises means for snap fitting said cover to said base.

11. The housing of claim 9 wherein said mounting means comprises bayonet locking means.

12. The housing of claim 1 wherein said cover is relatively rotatably mounted on said base.

13. The housing of claim 1 further comprising a plurality of connecting channels radially extending from said recess.

14. The housing of claim 13 further comprising a plurality of exit passageways, each of which is positioned to align with a different one of said connecting channels in said first relative position.

15. A filter housing for mounting on an ostomy pouch having a wall with an opening comprising a base having an entrance passageway, said base being sealed to the external surface of the pouch wall surrounding the opening with said entrance passageway aligned with the opening, said base having a portion which extends laterally outwardly beyond the seal, an exit passageway through said lateral portion of said base and a cover having filter receiving recess adapted to align with said entrance passageway and a connecting channel extending from said recess, said cover being mounted on said base for relative movement between a first position in which said connecting channel aligned with said exit passageway and a second position in which said connecting channel is remote from said passageway, said base having a disc-like configuration, said entrance passageway extending substantially axially through said base and said exit passageway being substantially parallel to said entrance passageway.

16. A filter housing for mounting on an ostomy pouch having a wall with an opening comprising a base having an entrance passageway, said base being sealed to the external surface of the pouch wall surrounding the opening with said entrance passageway aligned with the opening, said base having a portion which extends outwardly beyond the seal, an exit passageway through said portion of said base and a cover having a filter receiving recess adapted to align with said entrance passageway and a connecting channel extending from said recess, said cover being mounted on said base for relative movement between a first position in which said connecting channel aligns with said exit passageway and a second position at which said connecting channel is remote from said exit passageway, said housing further comprising a plurality of connecting channels radially extending from said recess and a plurality of exit passageways, each of said exit passageways being positioned to aligned with a different one of said connecting channels in said first relative position.

* * * * *